Figure 1:
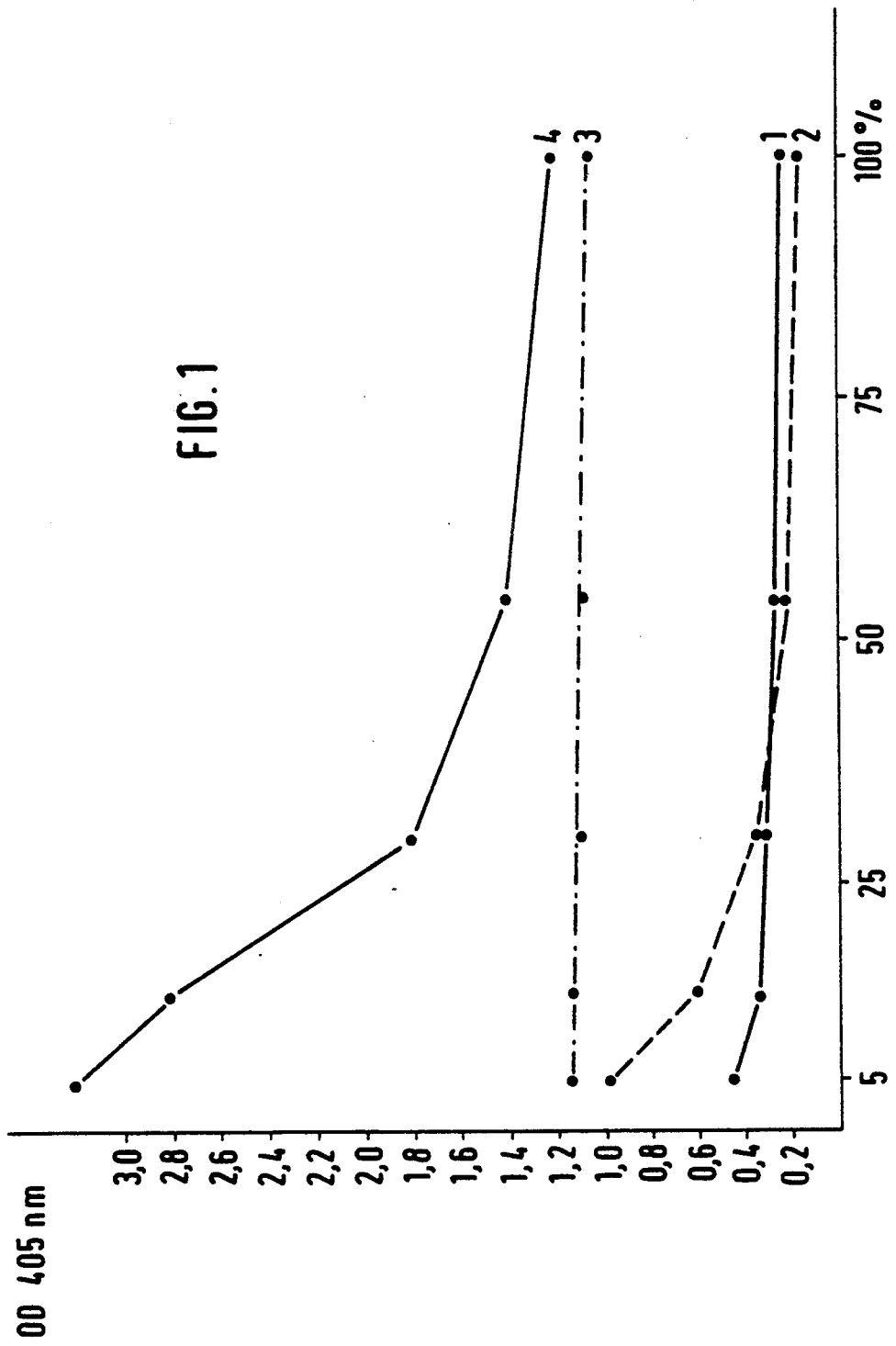

United States Patent [19]

Stief et al.

[11] Patent Number: 5,057,414
[45] Date of Patent: Oct. 15, 1991

[54] METHOD FOR THE DETERMINATION OF THE ACTIVITY OF SERINE PROTEASES OR SERINE PROTEASE INHIBITORS

[75] Inventors: Thomas Stief; Norbert Heimburger, both of Marburg, Fed. Rep. of Germany

[73] Assignee: Behringwerke Aktiengesellschaft, Marburg/Lahn, Fed. Rep. of Germany

[21] Appl. No.: 214,258

[22] Filed: Jul. 1, 1988

[30] Foreign Application Priority Data

Jul. 3, 1987 [DE] Fed. Rep. of Germany ....... 3722082

[51] Int. Cl.$^5$ .............................................. C12Q 1/56
[52] U.S. Cl. ........................................ 435/13; 435/23
[58] Field of Search ................... 435/13, 23, 184, 810

[56] References Cited

U.S. PATENT DOCUMENTS 4,493,891 1/1985 Travis ................................. 435/23
4,818,690 4/1989 Paques .

OTHER PUBLICATIONS

Beatty et al, "Kinetics of Association of Serine . . . ", *Journal of Biological Chemistry*, 255:3931–3934 (1980).
Verheijen et al, "Plasminogen Effectors", *Methods of Enzymatic Analysis*, vol. V, pp. 425–433 (1984).
Chemical Abstracts, vol. 96, No. 19, May 10, 1982, p. 517, Abstract 160021t, Allen, R. A., "An Enhancing Effect of . . . ".
Ichinose et al, "The Activation of Pro–Urokinase by . . . ", *Journal of Biological Chemistry*, 261:3486–3489 (1986).
Kluft et al, "Appropriate Millieu for the Assay . . . ", *Haemostasis*, 15:198–203 (1985).
Leung et al, "Poly-D-Lysine Dependent Inactivation . . . ", *Thrombosis Research*, 46:767–777 (1987).
Speiser et al, "Method for the Determination of Fast Acting Plasminogen Activator Inhibitor Capacity (PAI-CAP) in Plasma, Platelets and Endothelial Cell," *Thrombosis Research*, 44:503–515, 1986.
Chmielewska et al, Determination of Tissue Plasminogen Activator and Its "Fast" Inhibitor in Plasma, *Clinical Chemistry*, 32; 3:482–485, 1986.
Lawrence et al, Inactivation of Plasminogen Activator Inhibitor by Oxidants, *Biochemistry* 25; 21:6351–6355, 1986.
Shieh et al, The Reactive Site of Human $\alpha_2$-Antiplasmin, *Journal of Biological Chemistry*, 262; 13:6055–6059, 1987.
Shechter et al, Selective Oxidation of Methionine Residues in Proteins, *Biochemistry*, 14; 20:4497–4503, 1975.
Weiss et al, Long-Lived Oxidants Generated by Human Neutrophils: Characterization and Bioactivity, *Science* 222; Nov. 11, 1983, pp. 625–628.

*Primary Examiner*—Sam Rosen
*Attorney, Agent, or Firm*—Finnegan, Henderson, Farabow, Garrett, and Dunner

[57] ABSTRACT

The invention relates to a method for the determination of the activity of serine proteases and serine protease inhibitors in plasma or other biological fluids.

The only methods hitherto available for rapid and accurate determination of the content of serine proteases or serine protease inhibitors have been very time-consuming and methodologically demanding. In the method according to the invention for the determination of the activity of serine proteases or serine protease inhibitors, specific inhibitors are inactivated by addition of at least one oxidizing agent and, where appropriate, at least one detergent. The addition of an omega-aminocarboxylic acid enhances and observed effects when the serine protease is plasmin.

23 Claims, 9 Drawing Sheets

METHOD FOR THE DETERMINATION OF THE ACTIVITY OF SERINE PROTEASES OR SERINE PROTEASE INHIBITORS

The invention relates to a method for the determination of the activity of serine proteases or serine protease inhibitors in plasma or other biological fluids.

The body has two systems, which are in equilibrium, to protect itself both from blood loss and from thrombosis: the coagulation system and the fibrinolytic system. The interplay between the two systems ensures that insoluble fibrin polymers are produced initially to stop bleeding and, during wound healing, are broken down again by the lytic process of fibrinolysis.

Thrombin and plasmin are the key enzymes in both systems. Under physiological conditions, the dynamic equilibrium between the coagulation and fibrinolysis systems is under the control of the thromboplastic activity of thrombin and the thrombolytic activity of plasmin. The relevant inhibitors contribute to the equilibrium.

Plasmin is a relatively non-specific trypsin-like protease which is attributed with other physiological and pathophysiological functions besides dissolution of fibrin. Like many of the coagulation enzymes, plasmin circulates in the form of an inactive precursor, plasminogen, in the blood, and is activated only in response to certain stimuli. The conversion of plasminogen into plasmin is catalyzed by plasminogen activators.

Plasminogen can be activated by four different plasminogen activator systems:
1. A factor XII-dependent system,
2. a plasminogen activator isolated from Streptococci - streptokinase,
3. tissue plasminogen activator (t-PA) and
4. urinary plasminogen activator (u-PA or urokinase).

Only the two latter plasminogen activators, namely t-PA and u-PA, have physiological importance.

The plasminogen activators, as well as plasmin, are typical serine proteases. The available quantity of active plasmin and active plasminogen activators in the body is regulated by, inter alia, non-specific and specific inhibitors. Thus, for example, plasmin is inhibited non-specifically by alpha2-macroglobulin, inter-alpha inhibitor, $C_1$ esterase inhibitor and alpha$_1$-antitrypsin, as well as specifically by alpha$_2$-antiplasmin; the plasminogen activators are inhibited non-specifically by, inter alia, antithrombin III and alpha$_2$-antiplasmin, as well as specifically by plasminogen activator inhibitors.

These plasminogen activator inhibitors can be divided by immunological methods into at least three classes:
a) endothelial inhibitors: these include the inhibitors released from the endothelium and platelets, called PAI1 hereinafter;
b) placental inhibitors: these include the inhibitors released from the placenta and leukocytes, called PAI2 hereinafter;
c) heparin-dependent inhibitors: these include, for example, protein C inhibitor, which is called PAI3.

It is extremely important that the equilibrium between the components of the fibrinolysis system functions well and rapidly adjusts to the immediate needs of the body. Hyper- or hypofunction of the fibrinolytic activity may have fatal consequences, namely either hemorrhages or thromboses. In this connection, the inhibitors of the plasminogen activators appear to have particularly great clinical importance since, in particular, very high concentrations may lead to life-threatening complications.

Associations of this type have already been described in patients with deep leg vein thrombosis, acute myocardial infarct, bacteremia, liver diseases, inflammations of the pancreas, and cancers, as well as late in pregnancy and in patients with toxemia of pregnancy.

Hence there is very great clinical interest in the provision of reliable, rapid methods for the determination of various components of the fibrinolysis system in the plasma, serum or other biological fluids from patients in whom regulation of fibrinolysis is impaired. However, rapid and accurate determination of, for example, plasminogen activators or plasminogen activator inhibitors has not hitherto been possible because of the constant presence of specific or non-specific serine protease inhibitors.

The basic principle common to the methods hitherto known for determining PAI is to measure the activity of the inhibitor after addition of a defined quantity of a plasminogen activator, usually t-PA, by determining the remaining t-PA activity by provision of plasminogen and a chromogenic plasmin substrate, the conversion of which is then finally detected.

The accuracy of this functional determination of plasminogen activator inhibitors depends on eliminating all other inhibitors which may intervene in the reaction sequence described. As has been mentioned, plasmin, for example, is inhibited by at least five plasma proteins which have been described in detail. The methods described in the prior art for determining the plasminogen activator inhibitors thus require additional plasma separation steps such as, for example, a euglobulin precipitation, or require acidification and subsequent neutralization by high dilutions of the sample (Speiser et al., Thromb. Res. 44, 503–515, 1986; Chmielewska and Wiman, Clin.Chem. 32, 482–485, 1986). Both methods are relatively time-consuming and methodologically demanding.

Hence the object of the present invention was to make available a method with which the concentration of serine proteases and serine protease inhibitors in plasma, serum or other biological fluids can be determined rapidly and reliably.

This object is achieved according to the invention by adding at least one oxidizing agent and, where appropriate, at least one detergent to the sample which is to be examined for the content of serine proteases or serine protease inhibitors.

It has emerged, surprisingly, that the addition of a suitable oxidizing agent, where appropriate in conjunction with a detergent, depending on the test conditions, permits the interference-free determination of the activity either of plasminogen activator inhibitors, of tissue and of urinary plasminogen activator, of thrombin, of elastase or of plasminogen. Accurate determination of the said proteins requires that specific and non-specific plasmin inhibitors be quantitatively inactivated. Surprisingly, under the conditions according to the invention, alpha$_2$-antiplasmin is also nearly completely inactivated, whereas, for example, the plasminogen activator inhibitors, plasminogen activators and plasmin remain active. This result was completely surprising because in the prior art Lawrence and Loskutoff (Biochemistry 25, 6351–6355, 1986) report that they observed under their assay conditions an inactivation of the plasminogen activator inhibitors by hydrogen peroxide in concentrations of about 10 mM and chloramine T in a concentration of approximately 10 μM. This effect corresponds to expectations inasmuch as the plasminogen activator inhibitors belong to the family of serine protease inhibitors (serpins) whose archetype, namely alpha$_1$-protease inhibitor, contains an oxidizable methionine in the active center. Oxidation of this methionine results in a methionine sulfoxide, and the inhibitory functions are lost with the formation thereof. Lawrence and Loskutoff show, both for alpha$_1$-protease inhibitor and for plasminogen activator inhibitor, that the inactivation is reversible by treatment with dithiothreitol and methionine-sulfoxide-peptide reductase, i.e. under the conditions described therein the plasminogen activator inhibitor is demonstrably inactivated by oxidation. It was all the less to be expected that the complexes of plasminogen activator and plasminogen activator inhibitor produced in the reaction remain intact even under the oxidizing conditions according to the invention. It is surprising that the conditions according to the invention result in inactivation of alpha$_2$-antiplasmin, although it has recently been demonstrated that this inhibitor is resistant to oxidation (Shieh and Travis, J.Biol.Chem. 262, 6055–6059, 1987). Furthermore, it is very remarkable that the reaction of a non-inhibited plasminogen activator with its substrate, a natural or synthetic plasminogen, as well as the enzymatic reactions dependent thereon, take place undisturbed during the oxidation process.

Preferred oxidizing agents for the addition according to the invention are reagents which preferably oxidize methL ionine to methionine sulfoxide at pH 7.5–8.8. According to Schechter et al. (Biochem. 14, 4497–4503, 1975) these include halogeno amines and imides. However, substances from the group of reactive halogen derivatives, such as halogeno amides, imines or hydroxyls, including the salts thereof, would also be suitable. Oxidizing agents according to the invention are hydrogen peroxide, salts of peroxomonosulfuric acid or of peroxodisulfuid, oxidized glutathione, chloramine T, chloramine B, HOCl, salts of HOCl or N-chlorosuccinimide. Chloramine, HOCl or salts of HOCl are particularly preferred, corresponding to the natural secretion products of activated macrophages or polymorphonuclear neutrophils (Weiss et al. Science 222, 625–628, 1983).

According to Savige and Fontana (Methods in Enzymology 47, 453–459, 1977), suitable for the conversion of methionine into methionine sulfoxide are photooxidation promoted by dyestuffs (for example methylene blue, eosin, riboflavin and, particularly specifically, by hematoporphyrin at a pH below 7), as well as substances which contain positive halogen, such as N-bromosuccinimide; N-chlorosuccinimide; 2,4,6-tribromo-4-methylcyclohexadienone; BNPS-skatole (2-(nitrophenylsulfonyl)-3-methyl-3-bromoindolamine); chloramine T; t-butyl hypochlorite; trichloromethanesulfonyl chloride, furthermore 1-chlorobenzotriazole, iodobenzene dichloride in aqueous pyridine, pyridine bromide complexes, quinolines and, especially, 1,4-diazobicyclo[2.2.2]octanes in aqueous acetic acid.

It is expedient to use chloramine T for the oxidation, specifically in a concentration between 0.1 mM and 25 mM. The use of 0.5–4.5 mM chloramine T has proved to be particularly preferable.

The extent of the oxidizing action of chloramine T depends on the nature of the added detergent. It has proved particularly expedient to use polyoxyethylene ethers, for example $^R$Triton×100. On the one hand, the addition of Triton is intended to denature the interfering inhibitors, such as alpha$_2$-antiplasmin and antithrombin III, to such an extent that their reactive center is accessible to oxidation but, on the other hand, the activity of the enzymes involved in the detection, that is to say of the plasminogen activators and of the plasmin, must be retained. For this reason, the Triton concentration ought to be between 0.005 and 0.5% by weight, preferably 0.03–0.15% by weight.

On the one hand, the omega-amino carboxylic acids added according to the invention bring about very much slower inhibition of the plasmin by alpha$_2$-antiplasmin, so that alpha$_2$-antiplasmin can be more effectively inactivated by oxidation and, on the other hand, the activity of urokinase appears to be stimulated by the use of omega-amino carboxylic acids, preferably lysine, epsilon-amino-caproic acid, tranexamic acid or derivatives of these omega-amino carboxylic acids. Thus, the outcome of the addition of lysine to a sample whose plasminogen activator inhibitor content is to be determined without use of an oxidizing agent is an increase in the extinction by more than 100% compared with the sample without omega-amino carboxylic acid (see comparison experiments 1 and 2).

The addition of omega-amino carboxylic acids depends on the nature of the plasminogen activator used. Omega-amino carboxylic acids block the plasminogen activation by naturally occurring tissue plasminogen activator but have no effect on the plasminogen-activating capacity of urinary plasminogen activators or certain derivatives of tissue plasminogen activators prepared by synthesis or genetic manipulation.

It has proved to be preferable for carrying out the method according to the invention to use lysine in concentrations of 10 to 3,000 mM in the reaction mixture, particularly expediently in a concentration of 20 to 100 mM, in the same way as the use of epsilon-aminocaproic acid in a concentration of 2 to 500 mM, preferably 10–50 mM, or tranexamic acid in a concentration of 0.1 to 50 mM, preferably 1–5 mM. The use of the omega-amino carboxylic acids in these concentrations results in the reaction between plasmin and alpha$_2$-antiplasmin being reproducibly slowed down by a factor of at least 10.

For the determination of the activity of plasminogen activator inhibitors it is necessary to add to the sample at the start a defined quantity of plasminogen activator in order subsequently to be able to determine, from the difference between this defined quantity of plasminogen activator and the quantity of plasminogen activator still detectable after the reaction with the plasminogen activator inhibitor, the inhibitor concentration. Likewise, the determination of plasminogen requires an excess of plasminogen activators in order not to limit the plasminogen activation. In this connection, it is possible to use both tissue plasminogen activators and urinary plasminogen activator, or a natural and/or synthetic derivative of one of these plasminogen activators or even a combination of two or more proteins having plasminogen activator activity. The only prerequisite is that the plasminogen activator which is used is able to react with the plasminogen activator inhibitor or plasminogen which is to be determined. When a natural tissue plasminogen activator is used, it is expedient not to add an omega-amino carboxylic acid because the latter inhibits the plasminogenolytic activity of t-PA. However, in this case the tissue plasminogen activator activity should be stimulated by addition of soluble fibrin or fibrinogen fragments, polylysine or polysulfated polysaccharides.

The plasminogen activator substrate, which is likewise made available for the determination of the activity of plasminogen activator inhibitors and plasminogen activators, can be natural plasminogen or one of its natural or synthetic derivatives. It is merely necessary for the plasminogen which is used either to result, after its activation, in an active plasmin which can convert a chromogenic plasmin substrate in a subsequent reaction, or to result itself, after the activation by the plasminogen activator, in a measurable conversion product. It is preferred to use plasminogens without an alpha$_2$-antiplasmin-binding site such as, for example, miniplasminogen.

When the method according to the invention is used to determine the activity of serine proteases and serine protease inhibitors, it is possible for the conversion of substrates whose conversion is measurable to take place at two different levels.

A. In a preferred manner, it is possible to use for the determination of the activity of plasminogen activator inhibitors and plasminogen activators a non-chromogenic plasminogen activator substrate, that is to say plasminogen or any of its natural or synthetic derivatives, which, after activation by the remaining plasminogen activator, catalyzes the conversion of a second substrate. The solutions used for the assay ought to have plasminogen concentrations of 2.5 to 20 CTA-U/ml (1 CTA-U=278 pmol of plasminogen), preferably between 5 and 10 CTA-U/ml, in a buffered solution which expediently contains 50 to 150 mM Tris-HCl, pH 7.5 to pH 9.5, up to 100 mM sodium chloride, 1% by weight of crossi linked polypeptides, up to 0.2% by weight of $^R$Triton×100 and, where appropriate, small quantities (about 10 pg/ml) of alpha$_2$-antiplasmin. The alpha$_2$-antiplasmin acts to neutralize spontaneously formed plasmin, especially during storage of the solution. It does not interfere in the subsequent assay, since both it and the endogenous alpha$_2$-antiplasmin are inactivated by the added oxidizing agent. In a preferred manner, the oxidizing agent is chloramine T in a concentration of 0.5 to 15 mM. When plasminogen activators whose plasminogenolytic activity is not inhibited by addition of omegaamino carboxylic acid are used, it is possible additionally to add at least one omega-amino carboxylic acid, preferably tranexamic acid in a concentration of 0.2 to 5 mM. Furthermore, a solution of a chromogenic plasmin substrate, preferably 2 to 20 mM H-D-Val-Leu-Lys-p-nitroanilide (pNA). 2 HCl, H-D-Phe-Tyr-Arg-ANBA . 2 HCl (ANBA =-NH-C$_6$H3-p-N02-m-COOH) or H-D-Nva-CHA-Lys-pNA 2 HCl in distilled water or, for measurements in linear kinetics, in a solution which suppresses the PA activity without affecting the plasmin activity, such as, for example, 200 to 2,000 mM NaCl or KCl, 100 to 1,000 mM CsCl or 10 to 100 mM Na$_2$S0$_3$, should be added to the sample.

B. The procedure when tissue plasminogen activators are used is as described under A. The plasminogenolytic activity is stimulated by addition of fibrin, polysulfated polysaccharides, polylysine, soluble fibrin or fibrinogen fragments.

An alternative embodiment of the method according to the invention for the determination of plasminogen activator inhibitors provides for the use of a chromogenic plasminogen activator substrate, preferably pyro-Glu-Gly-Arg-p-nitroanilide for the determination with urokinase, or H-D-Ile-Pro-Arg-p-nitroanilide for the determination with tissue plasminogen activator. It is expedient to provide between 1 and 20 mM, preferably 2 to 5 mM, of one of these chromogenic plasminogen activator substrates in a buffer solution containing, for example, 50 to 150 mM Tris-HCl, pH 7.5 to 9.5, 1 μM aprotinin, 1% by weight of crosslinked polypeptides ($^R$Haemaccel) and up to 0.05% of $^R$Triton×100.

The most important use of the method according to the invention is without doubt the determination of the activity of plasminogen activator inhibitors. For this purpose, either a plasminogen activator, a plasminogen activator substrate whose conversion can be detected, at least one oxidizing agent and, where appropriate, at least one detergent plus, where appropriate, at least one omega-amino carboxylic acid are added to the sample to be investigated, or else, alternatively, a plasminogen activator, a first plasminogen activator substrate, a second substrate for the conversion product of the first substrate, whose conversion can be detected, at least one oxidizing agent, and, where appropriate, at least one detergent plus, where appropriate, at least one omega-amino carboxylic acid or, where appropriate, soluble fibrin or fibrinogen degradation products are added, and the quantity of plasminogen activator inhibitor contained in the sample is measured as a function of the quantity of plasminogen activator which is added and not inhibited.

The various plasminogen activator inhibitors differ in sensitivity to the oxidizing agents. This makes it . possible for oxidation-resistant plasminogen activator inhibitors such as PAI2 to be determined selectively. Likewise, the determination of oxidation-sensitive plasminogen activator inhibitors is made possible by measurements on the same sample, on the one hand by the method described above and, on the other by the method described hereinafter for the determination of oxidation-resistant plasminogen activator inhibitors, by determining the difference between the total content of plasminogen activator inhibitors in the sample and the content of oxidation-resistant plasminogen activator inhibitors in the sample. For the determination of oxidation-resistant plasminogen activator inhibitors such as PAI2, first at least one oxidizing agent and, where appropriate, at least one detergent plus, where appropriate, at least one omega-amino carboxylic acid or a substance stimulating t-PA are added to the sample, and then either a plasminogen activator, a plasminogen activator substrate whose conversion can be detected, or else, alternatively, a plasminogen activator, a first plasminogen activator substrate, a second substrate for the conversion product of the first substrate, whose conversion can be detected, are added, and the quantity of oxidation-resistant plasminogen activator inhibitor contained in the sample is measured as a function of the quantity of plasminogen activator which is added and not inhibited.

The method according to the invention also allows the quantification of the quantities of single-chain urinary plasminogen activator (scu-PA), two-chain u-PA and single- and two-chain t-PA present in the plasma, by incubation of the PA-containing samples with, according to the invention, omega-amino carboxylic acid in the case of u-PA or of a t-PA stimulator, oxidizing agent and, where appropriate, detergent, as well as with defined quantities of plasminogen and of a plasmin substrate whose conversion can be detected. It is expedient for the detection of scu-PA to convert the latter into the more active two-chain form. This is possible, after the preliminary plasma oxidation, by addition of kallikrein, or generation thereof by addition of a surface activator (such as ellagic acid or sulfatide). This kallikrein can—like plasmin—convert the single-chain form into the two-chain form of urokinase.

The determination of plasminogen is carried out in analogy to the PA determination. In this case, the plasminogen-containing biological fluid is likewise treated with an oxidizing agent such as, for example, chloramine T and with a detergent; additionally made available in the reaction mixture are plasminogen activators and a plasmin substrate whose conversion is detectable. After all the specific and non-specific plasmin inhibitors have been inactivated, activation of the quantity of plasminogen which is to be measured results in subsequent conversion of the detectable plasmin substrate.

The invention is explained in more detail by the Figures, Examples and Comparison Experiments hereinafter.

FIG. 1 shows elimination of the alpha$_2$-antiplasmin action in the plasma system. The figure shows the effect of oxidizing agents and/or omega-amino carboxylic acids on the conversion of a chromogenic plasmin substrate. The experiment on which the figure is based is described in Comparison Example 1.

Figure 2:
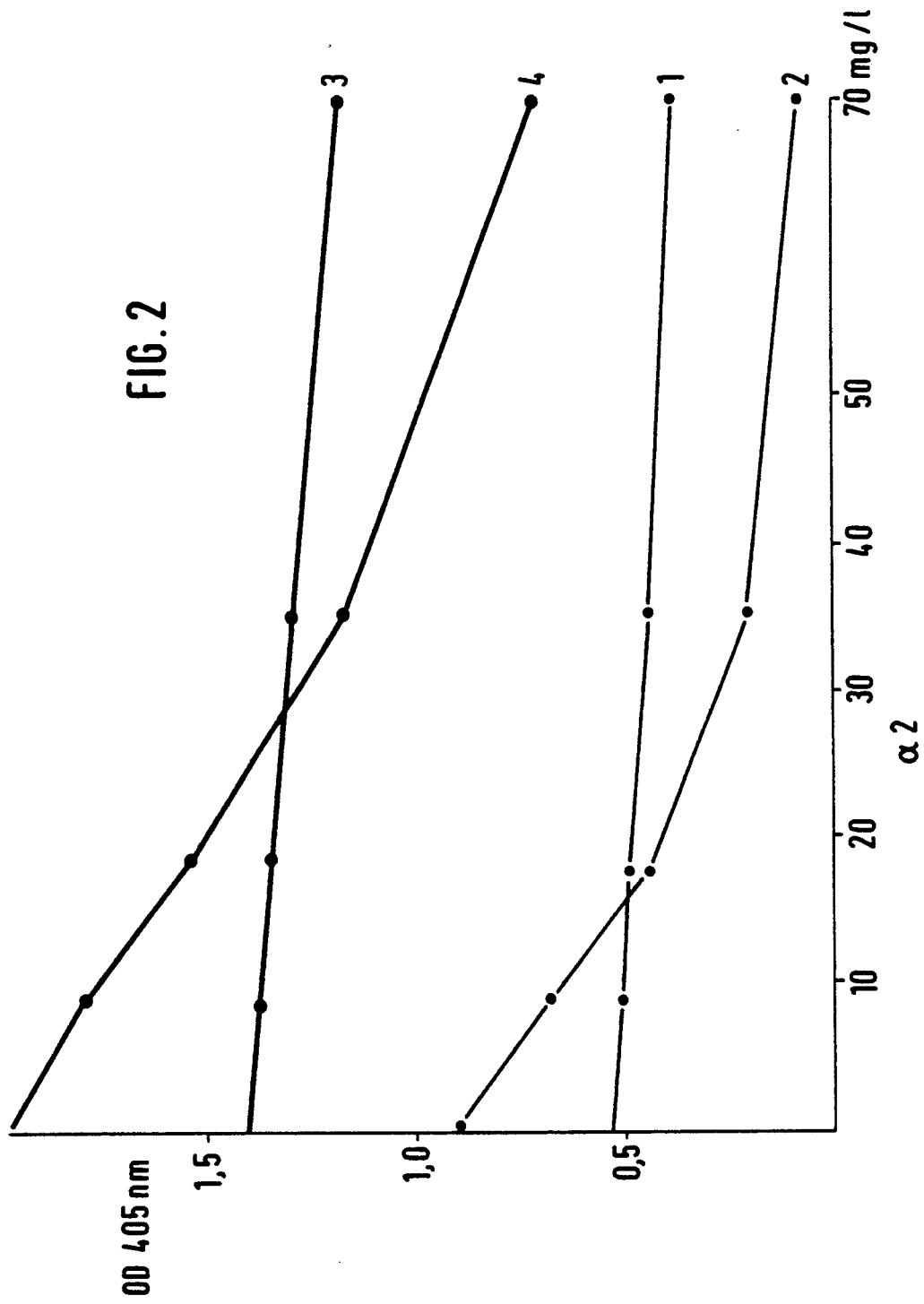

FIG. 2 shows elimination of the alpha$_2$-antiplasmin action in the buffer system. The dependence of the conversion of a chromogenic substrate in the presence of defined quantities of alpha$_2$-antiplasmin, which are between 0 and 100% of the quantities present physiologically, after addition of the substances according to the invention is shown. The experiment on which the figure is based is described in Comparison Example 2.

Figure 3:
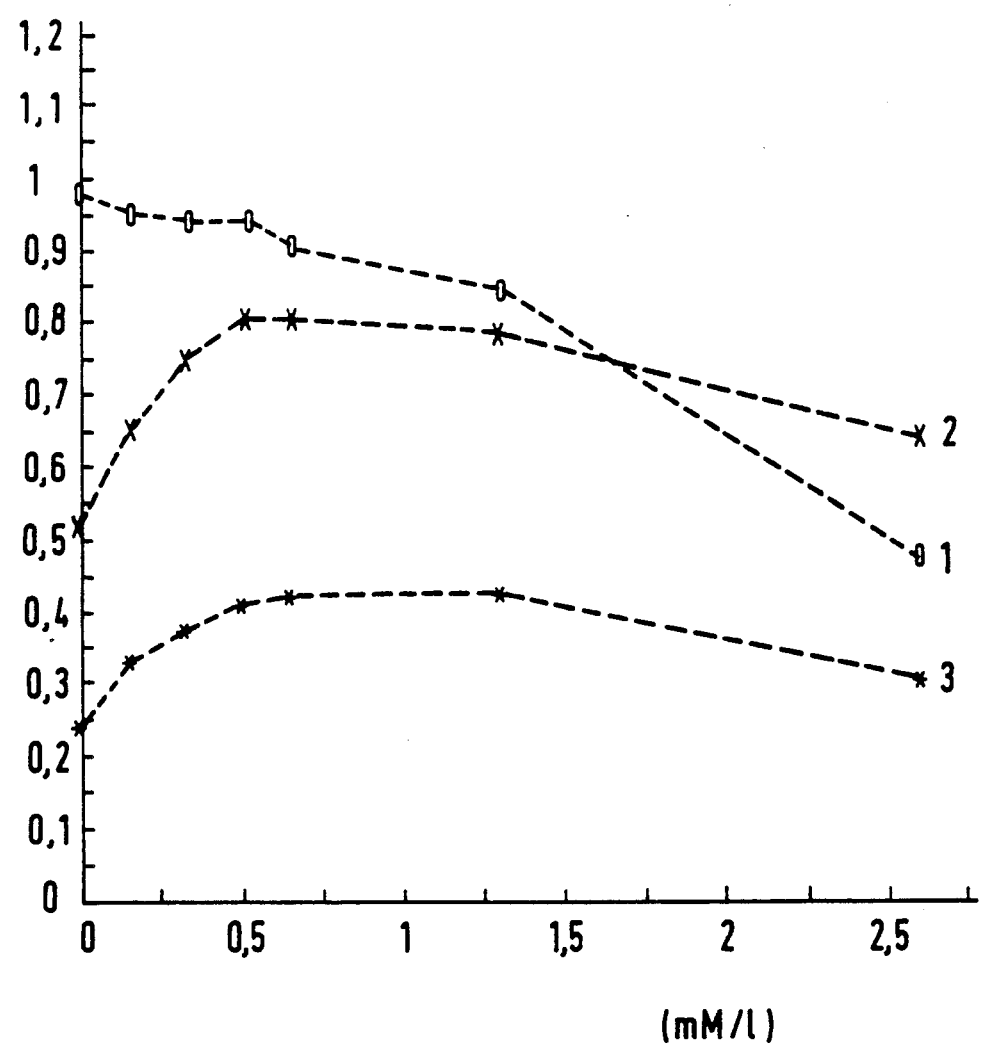

FIG. 3 shows the dependence of the stability of the PAI/u-PA complex on the chloramine T concentration. The figure demonstrates the stability of the PAI/u-PA complex even at concentrations above 2 mmol of chloramine T/l. The experiment on which the figure is based is described in Comparison Example 3.

Figure 4A:
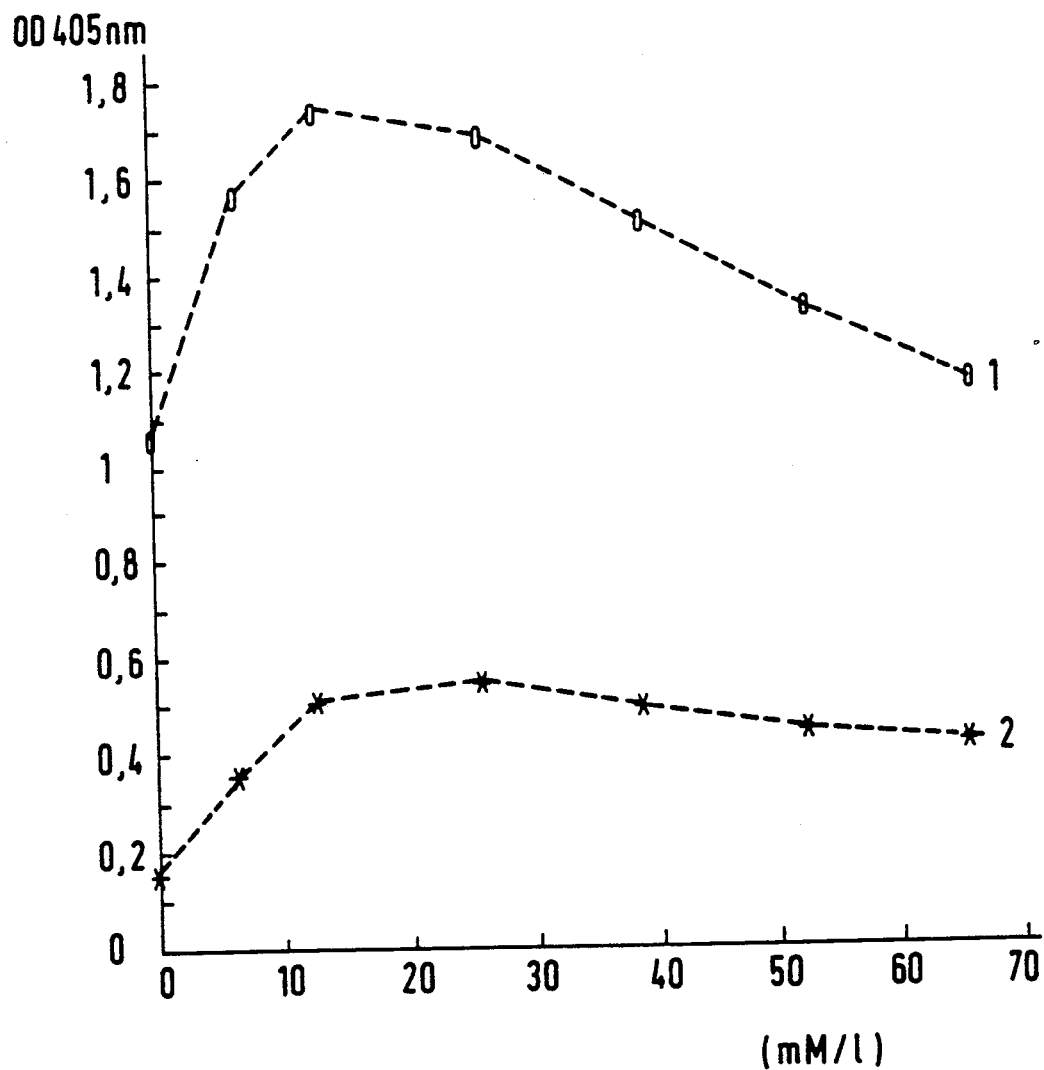
Figure 4B:
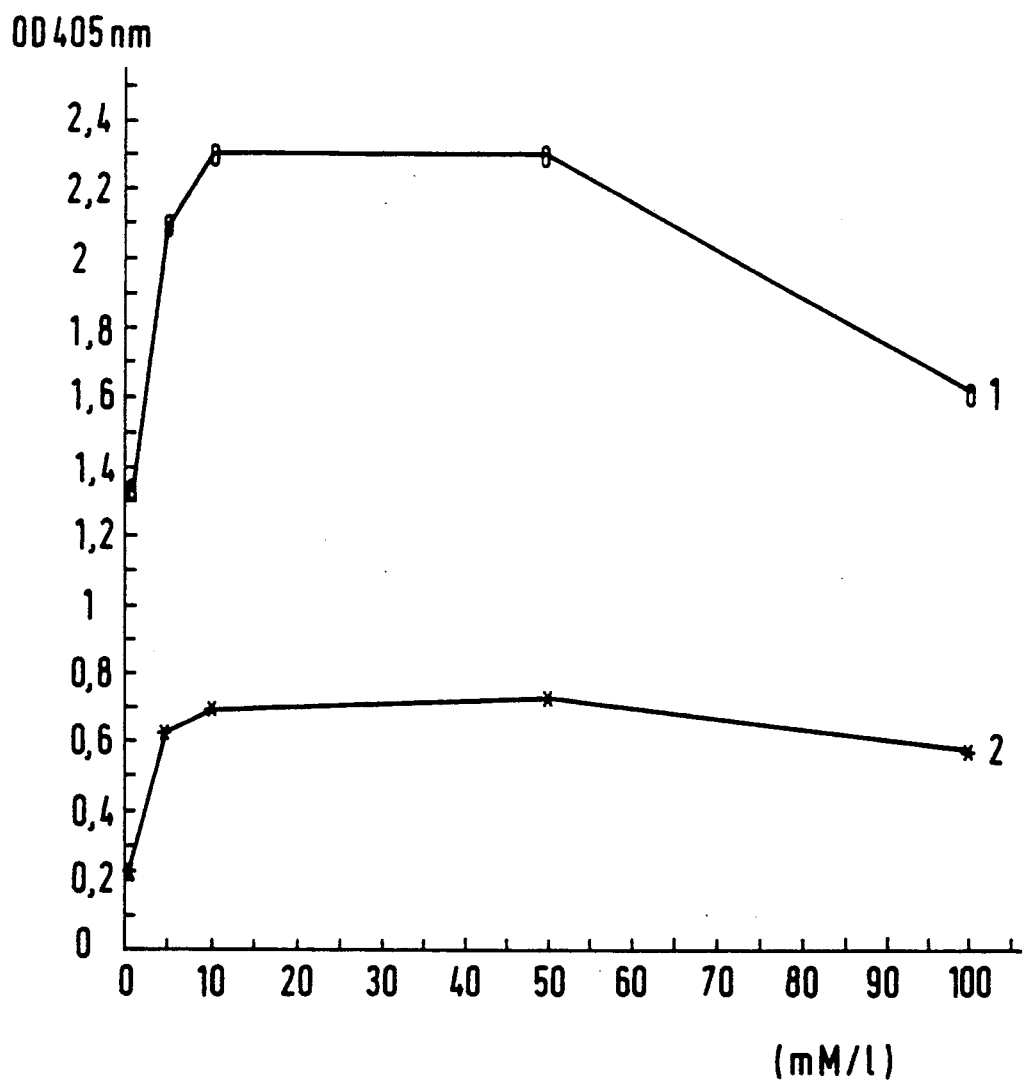
Figure 4C:
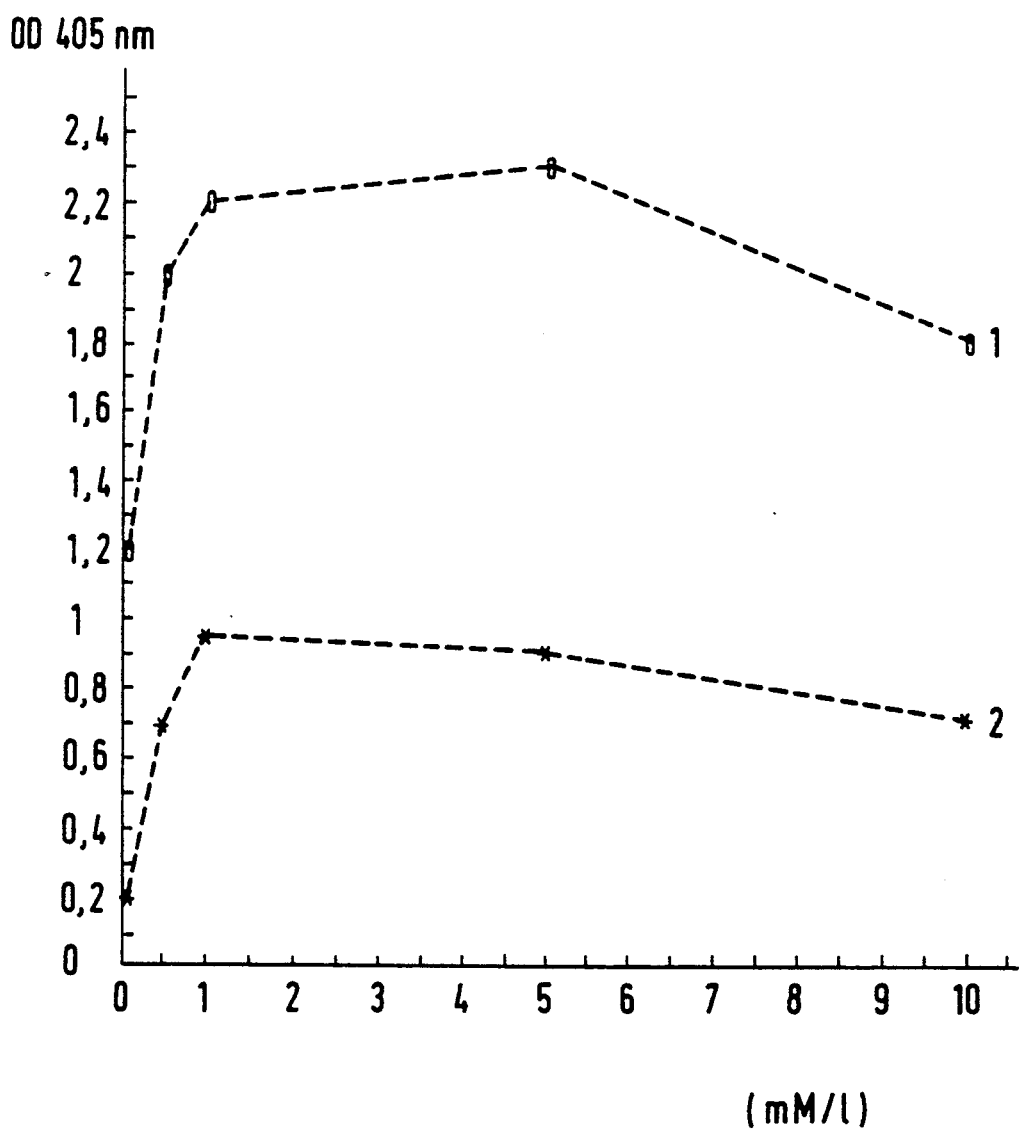

FIG. 4 shows the dependence of the plasmin activity on the concentration of omega-amino carboxylic acid added. The figures show the effect of various omega-amino carboxylic acids on the activity of plasmin in the test system according to the invention. Specifically, FIG. 4a shows the effect of lysine, FIG. 4b shows the effect of epsilon-aminocaproic acid, FIG. 4c shows the effect of tranexamic acid. The experiments which correlate with the figures are described in comparison experiment 4a–c.

Figure 5:
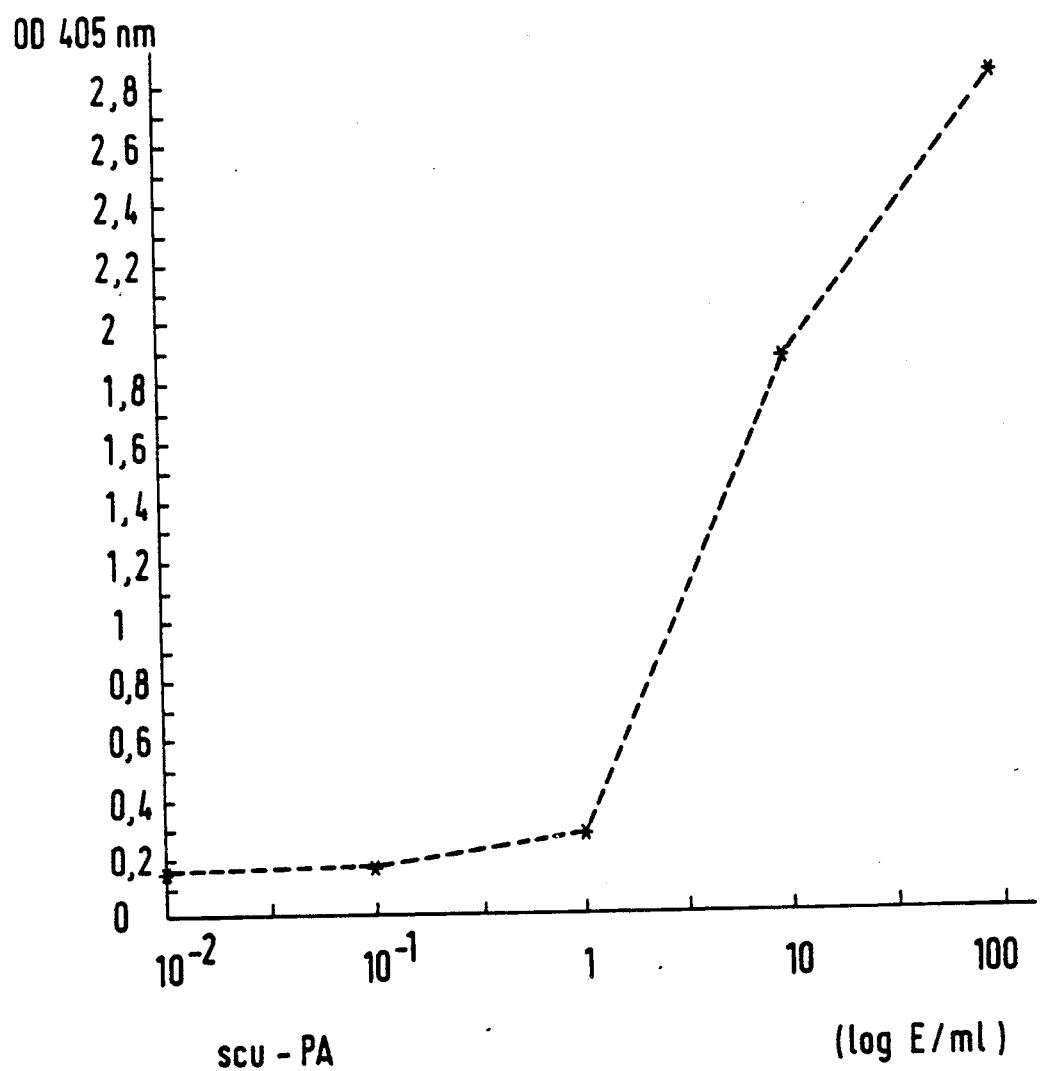

FIG. 5 shows the determination of single-chain urinary plasminogen activator in plasma. The figure shows the correlation between the optical density generated by conversion of a chromogenic substrate and the scu-PA content of supplemented normal plasma. The experimental procedure is described in Example 7.

Figure 6:
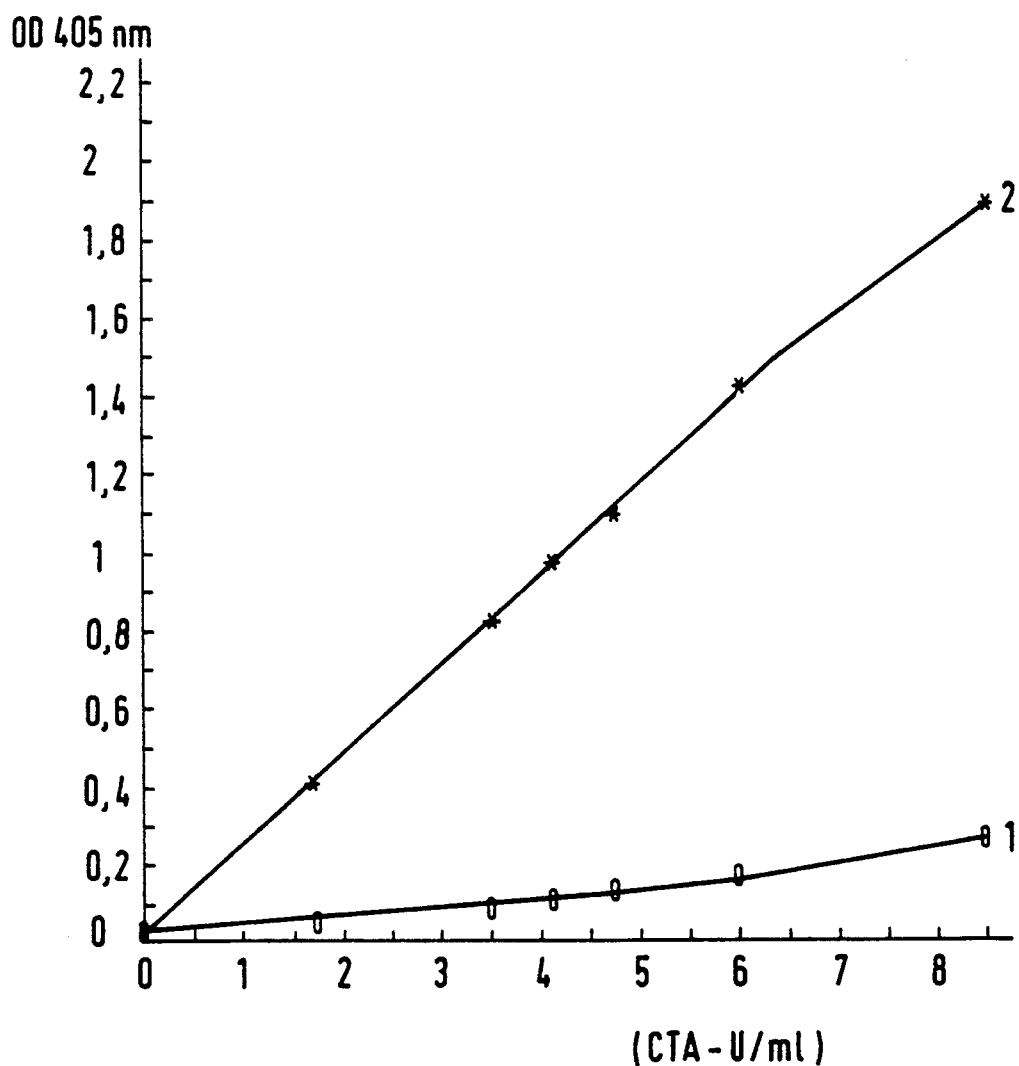

FIG. 6 shows the determination of the plasminogen concentration in plasma. The figure shows the comparison of untreated plasma samples with plasma samples which have different plasminogen contents and have been treated according to the invention with chloramine T, tranexamic acid and detergent. The basic experiment is described in Example 8.

Figure 7:
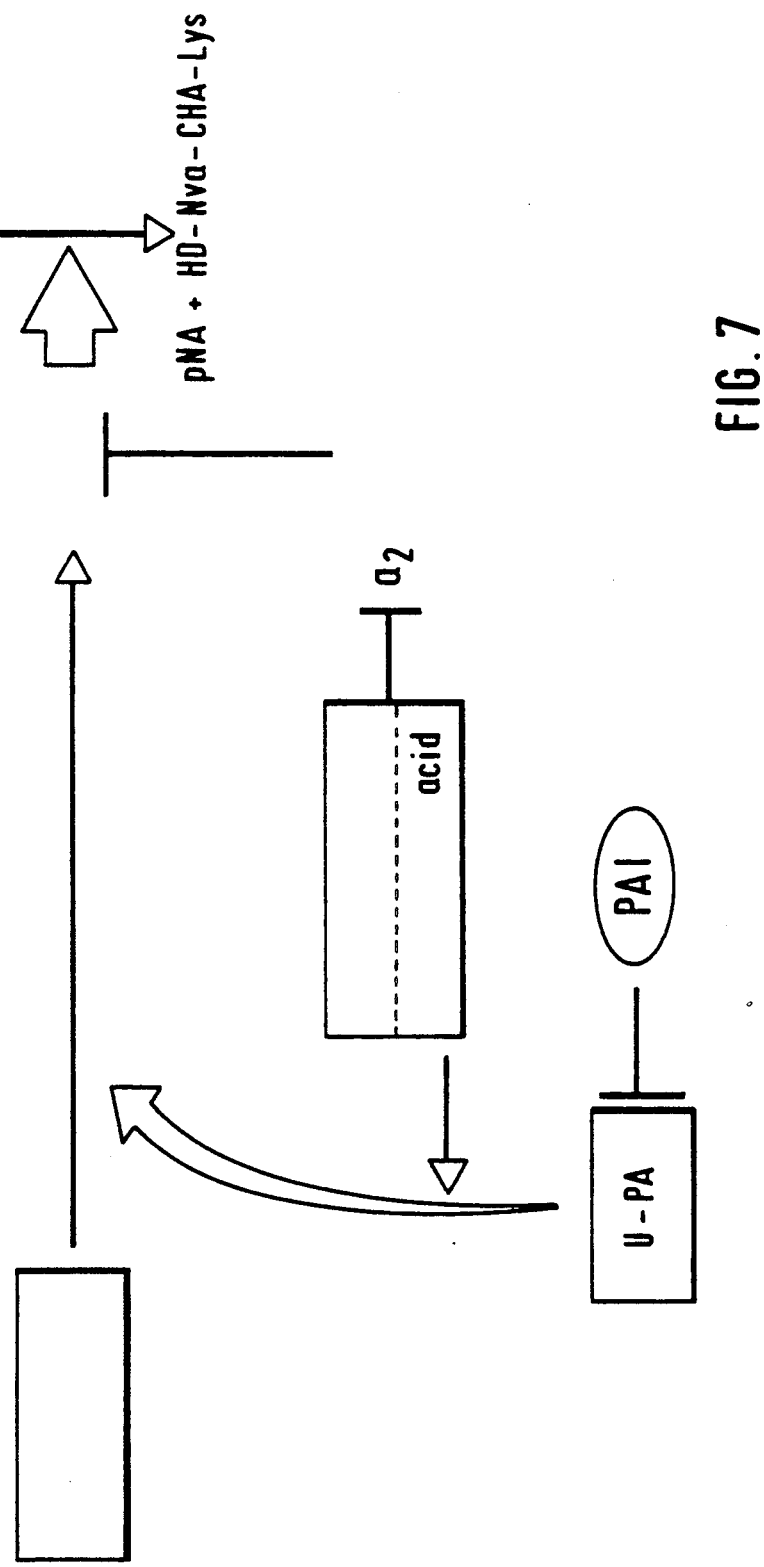

FIG. 7 shows the principle of the assay for the determination according to the invention of PAI (PA). Substance added to he reaction mixture ae depicted in boxes.

The Examples and Comparison experiments hereinafter were carried out using the following solutions; unless otherwise indicated, the statement "%" denotes "% by weight".

| (A) Basic buffer | |
|---|---|
| Tris-HCl pH 8.5 | 50 mM |
| Sodium chloride | 100 mM |
| Crosslinked polypeptides | 1% |
| $^R$Triton × 100 | 0.05% |
| NaN$_3$ | 0.01% |
| (B) Oxidizig reagent | |
| Chloramine T | 40 mM |
| (C) Plasminogen activator reagent | |
| Urokinase | 5 IU/ml |
| Tris-HCl pH 8.8 | 50 mM |
| Sodium chloride | 100 mM |
| Crosslinked polypeptides | 1% |
| $^R$Triton × 100 | 0.1% |
| NaN$_3$ | 0.01% |
| (D) Plasminogen activator substrate reagent | |
| Tris-HCl pH 8.5 | 50 mM |
| Aprotinin | 1 μM |
| Crosslinked polypeptides | 1% |
| $^R$Triton × 100 | 0.05% |
| pyro-Glu-Gly-Arg-p-nitroanilide | 2 mM |

When tissue plasminogen activators are used it is possible to replace pyro-Glu-Gly-Arg-p-nitroanilide by H-D-Ile-Pro-Arg-p-nitroanilide.

| (E) Plasmin substrate reagent | |
|---|---|
| Tris-HCl pH 8.5 | 50 mM |
| Crosslinked polypeptides | 1% |
| $^R$Triton × 100 | 0.05% |
| H-D-Phe-Tyr-Arg-ANBA · 2 HCl | 2 mM |

It is possible to choose to replace H-D-Phe-Tyr-Arg-ANBA . 2 HCl by another chromgenic plasmin substrate (such as, for example, H-D-Nva-CHA-Lys-pNA).

| (F) Plasminogen reagent | |
|---|---|
| Tris-HCl pH 8.5 | 50 mM |
| Crosslinked polypeptides | 1% |
| $^R$Triton × 100 | 0.05% |
| Tranexamic acid | 15 mM |
| Plasminogen | 20 CTA-U/ml |

When tissue plasminogen activators are used or detected, tranexamic acid is replaced by t-PA stimulator (1mg/ml).

| (G) Basic buffer U | |
|---|---|
| Tris-HCl pH 8.4 | 100 mM |
| Crosslinked polypeptides | 1% |
| NaCl | 100 mM |
| $^R$Triton × 100 | 0.1% |
| NaN$_3$ | 0.01% |

COMPARISON EXPERIMENT 1

50μl of a plasma which is deficient in alpha$_2$-antiplasmin and has been prepared by immunoadsorption, as well as 1:2, 1:4 and 1:8 mixtures of this deficient plasma with normal plasma, where mixed with 200 μl or solution C (plasminogen activator reagent). Identical parallel samples were mixed with oxidizing agent and/or an omega-amino carboxylic acid, as indicated in the Table which follows:

TABLE 1

| Sample | Oxidizing agent 5% (NH4)2S2O8 in distilled water | omega-amino carboxylic acid 10% lysine in distilled water | H2O |
|---|---|---|---|
| 1 | 50 μl | | 100 μl |
| 2 | | | 150 μl |
| 3 | 50 μl | 100 μl | |
| 4 | | 100 μl | 50 μl |

200 pl of a 3 mM solution of H-D-Phe-Tyr-Arg-ANBA . 2 HCl in solution A and 500 pl of a plasminogen solution (2 CTA-U/ml) in solution A were added to the samples, the mixtures were incubated at 37° C. for 20 min, subsequently 100 μL of 8.5 M acetic acid were used to stop, and the extinction at 405 nm was determined. FIG. 1 shows the comparison of the extinctions of the various samples. It is evident that addition of lysine increases the activity of urokinase by more than 100%. At the same time, comparison of the samples shows that, owing to the addition of ammonium peroxodisulfate, the conversion of the chromogenic plasmin substrate does not depend on the quantity of alpha$_2$-antiplasmin contained in the plasma.

COMPARISON EXPERIMENT 2 Elimination of the alpha$_2$-antiplasmin action in the buffer system

A solution of 70 mg/1 alpha$_2$-antiplasmin in solution A (basic buffer), which corresponds to the physiological concentration, was diluted 1:1, 1:2, 1:4 and 1:8. 50 pl of each dilution were mixed with 200 μl of solution C (plasminogen activator reagent) and then subsequently treated as in Comparison Experiment 1.

TABLE 2

| Sample | Oxidizing agent 5% (NH4)2S2O8 in distilled water | omega-amino carboxylic acid 10% lysine in distilled water | H2O |
|---|---|---|---|
| 1 | 50 μl | | 100 μl |
| 2 | | | 150 μl |
| 3 | 50 μl | 100 μl | |
| 4 | | 100 μl | 50 μl |

The result of this Comparison Experiment is shown in FIG. 2.

COMPARISON EXPERIMENT 3 Dependence of the stability of the PAI/u-PA complex on the chloramine T concentration

50 μl of various samples, namely either basic buffer A (1) or PAI-deficient plasma (2) and PAI-rich plasma (3) were incubated with 200 μl of solution C (plasminogen activator reagent) at 23° C. for 10 min. After addition of 500 μl of solution A (basic buffer), 50 μl of chloramine T of various concentrations, 300 μl of solution E (plasmin substrate reagent) and 100 μl of solution F (plasminogen reagent), the mixtures were incubated at 37° C. for 15 min. Substrate conversion was stopped by addition of 100 μl of 8.5 M acetic acid, and the extinction at 405 nm was determined. The oxidizing agent chloramine T used in this experiment was employed in solutions of the following concentrations.

TABLE 3

| Concentration of the chloramine T solution (mM) | Chloramine T concentration in the reaction mixture (mM) |
|---|---|
| 0 | 0 |

TABLE 3-continued

| Concentration of the chloramine T solution (mM) | Chloramine T concentration in the reaction mixture (mM) |
|---|---|
| 3.7 | 0.15 |
| 7.5 | 0.31 |
| 15.5 | 0.64 |
| 23.5 | 0.98 |
| 31 | 1.3 |
| 62 | 2.58 |

The result of this Comparison Experiment is shown in FIG. 3. In this, (1) corresponds to the curve for basic buffer (2) corresponds to the curve for PAI-deficient plasma and (3) corresponds to the curve for PAI-rich plasma.

It is evident from the figure that even chloramine T concentrations above 2 mM do not result in cleavage of the PAI/u-PA complexes: the course of the curve obtained for the PAI-deficient plasma is always proportional to the curve for PAI-rich plasma. However, the stability of urokinase depends on the presence of methionine-containing plasma proteins; urokinase in the pure buffer system is attacked by as little as 1 mM chloramine T.

COMPARISON EXPERIMENT 4 Dependence of plasmin activity on the concentration of omega-amino carboxylic acids added

The concentration range in which various omega-amino carboxylic acids show their action according to the invention was determined by carrying out various comparison experiments with a) lysine b) epsilon-aminocaproic acid, and c) treanexamic acid in accordance with a uniform scheme. For this, in each case 50 μof sample, namely either solution A (basic buffer) or citrate-treated plasma, were mixed with b 200 μl of solution C (plasminogen activator reagent), 500 μl of solution A (basic buffer), 200 μl of solution E (plasmin substrate reagent), 100 μl of modified solution F (plasminogen reagent), 100 μl of modified solution F (plasminogen reagent) which contained no omega-amino carboxylic acid, and subsequently 100 ∞l of the various omega-amino carboxylic acids corresponding to the Example given below. The mixture was incubated at 37° C. for 20 mion, and the reaction was then stopped by addition of 100 μl of 8.5 M acetic acid, and the extinction at 405 nm was determined.

a) comparison Experiment for Lysine

TABLE 4

| Concentration of the added lysine solution (mM) | Lysine concentration in the reaction mixture (mM) |
|---|---|
| 0 | 0 |
| 75 | 6.5 |
| 150 | 13 |
| 300 | 26 |
| 450 | 39 |
| 600 | 52 |
| 750 | 65 | b) Comparison Experiment for epsilon-aminocaproic acid

TABLE 5

| Concentration of the added epsilon-aminocaproic acid solution (mM) | Epsilon-aminocaproic acid concentration in the reaction mixture (mM) |
| --- | --- |
| 0 | 0 |
| 55 | 4.8 |
| 110 | 9.5 |
| 550 | 47.8 |
| 1100 | 95 | c) Comparison Experiment for tranexamic acid

TABLE 6

| Concentration of the added tranexamic acid stock solution (mM) | Tranexamic acid concentration in the reaction mixture (mM) |
| --- | --- |
| 0 | 0 |
| 5.5 | 0.48 |
| 11 | 0.95 |
| 55 | 4.8 |
| 110 | 9.5 |

Drawings 4a to 4c show the results of the Comparison Experiments. In each of these, curve 1 represents the values obtained for the buffer sample, whereas curve 2 depicts the curve obtained with the citrate-treated plasma.

The optimal omega-amino carboxylic acid concentrations determined in these Comparison Experiments were employed when carrying out the method according to the invention.

EXAMPLE 1 Determination of plasminogen activator inhibitor in plasma or serum or other biological fluids using a chromogenic urokinase substrate 50 μl of plasma were incubated with 200 μl of solution C (plasminogen activator reagent) at 23° C. for 10 min.

After addition of 500 μl of solution A (basic buffer), 50 μl of solution B (oxidizing reagent) and 200 μl of solution D (plasminogen activator substrate reagent,) the mixture was incubated at 37° C. for 200 min. The substrate conversion was stopped by addition of 100 μl of 8.5 M acetic acid and the extinction at 405 nm was determined.

EXAMPLE 2 Determination of plasminogen activator inhibitor in plasma or serum or other biological fluids using a chromogenic plasmin substrate and plasminogen 50 μl of plasma were incubated with 200 μl of solution C (plasminogen activator reagent) at 23° C. for 10 min. After addition of 500 μl of solution A (basic buffer), 50 μl of solution B (oxidizing reagent) and 200 μl of solution E (plasmin substrate reagent) and 100 μl of solution F (plasminogen reagent), the mixture was incubated at 37° C. for 15 min or at 23° C. for 30 min. The substrate conversion was stopped by addition of 100 μl of 8.5 M acetic acid, and the extinction at 405 nm was determined.

EXAMPLE 3 Kinetic determination of plasminogen activator inhibitor in plasma or serum or other biological fluids Preincubation of 50 μl of sample with 200 μl of a variant of solution C (plasminogen activator dissolved in basic buffer U) at 37° C. for five minutes was followed by addition of 200 μl of a variant of plasminogen reagent (F), composed of 100 mM Tris-HCl pH 8.4, crosslinked polypeptides 1%, $^R$Triton×100 0.1%, 100 mM NaCl without tran-examic acid, $NaN_3$ 0.01% (basic buffer U) with 10 CTA-U/ml plasminogen and 200 μl of distilled water with 10 mM chloramine T, 3 mM tranexamic acid to the reaction mixture. The mixture was incubated at 37° C. for 5 min, and 500 μl of 0.6 mM chromogenic plasmin substrate HD-Nva-CHA-Lys-pNA in 480 mM NaCl (or, as a substitute, 200 mM CsCl) were added. The resultant linear change in extinction, delta A/min, at 405 nm was followed. The values found for normal plasma were about 0.2/min.

As an alternative to the kinetic measurement, it was possible to stop the chromogenic substrate conversion by addition of 100 μl of 8.5 M acetic acid after four minutes (37° C.), which resulted in an end point determination based on linear reaction kinetics.

EXAMPLE 4a Determination of the plasminogen activator inhibitor of the placental type (PAI2) using a chromogenic plasminogen activator substrate 50 μl of sample were incubated with 500 μl of solution A (basic buffer) and 50 μl of solution B (oxidizing reagent) at 37° C. for 10 min, and then the reaction mixture was mixed with 200 μl of solution C (plasminogen activator reagent), and the mixture was incubated at 37° C. for 5 min. The substrate conversion was started by addition of 200 μl of solution D (plasminogen activator substrate reagent), and the mixture was incubated at 37° C. for 200 min. After the reaction was stopped by 100 μl of 8.5 M acetic acid, the extinction at 405 nm was determined.

EXAMPLE 4 Determination of the plasminogen activator inhibitor of the placental type (PAI2) using a chromogenic plasmin substrate 50 μl of sample were incubated with 500 μl of solution A (basic buffer) and 50 μl of solution B (oxidizing reagent) at 37° C. for 10 min. Addition of 200 μl of solution C (plasminogen activator reagent) was followed by incubation at 37° C. for 5 min. The substrate conversion was started by addition of 200 μl of solution E (plasmin substrate reagent) and 100 μl of solution F (plasminogen reagent) and the mixture was incubated at 37° C. for 15 min. After addition of 100 μl of 8.5 M acetic acid, the extinction at 405 nm was determined.

Evaluation of the experiment shows that PAI1 is nearly completely inactivated when the oxidation is carried out before addition of the plasminogen activator reagent. In contrast to this, PAI2 is less sensitive to oxidation and can thus be determined selectively.

EXAMPLE 5a Determination of PAI2 via preincubation with polycation-containing PA reagent The assay procedure was that described in Example 3. The only difference was the content of protamine chloride (100 U/ml) or polylysine (500 μg/ml) in the plasminogen activator reagent, so that only PAI2 (and not PAI1) was measured.

EXAMPLE 5 Determination of the plasminogen activator inhibitor of the placental type (PAI2) via preincubation with single-chain tissue plasminogen activator 50 μl of sample were mixed with 100 μl of a solution of 100 I.U. of single-chain tissue plasminogen activator in solution A (basic buffer) and the mixture was incubated at 37° C. for 15 min. The procedure after addition of 200 μl of solution C (plasminogen activator reagent) was as in Example 1 or 2. Single-chain t-PA reacts with PAI2, in contrast to PAI1, very slowly, so that the residual content of PAI (=PAI2) can be determined by addition of two-chain PA.

EXAMPLE 6 Determination of the plasminogen activator inhibitor of the endothelial type (PAI1) using tissue plasminogen activator and a chromogenic plasmin substrate, and detection of the activity of tissue plasminogen activator in plasma.

50 μl of sample were incubated with 200 μl of a modified solution C (plasminogen activator reagent), which contained 25 units/ml single-chain tissue plasminogen activator in place of urokinase, at 23° C. for 15 min. After addition of 500 μl of solution A (basic buffer), 20 μl of solution B (oxidizing reagent), 200 μl of solution E (plasmin substrate reagent) and 100 μl of a modified solution F which, on the one hand, contained no tranexamic acid and, on the other hand, contained fibrinogen fragments, which had been prepared by plasmin cleavage in the presence of 5 mM EDTA, in a concentration of 1200 pg/ml of solution F, the mixture was incubated at 37° C. for 15 min. The substrate mixture was stopped by addition of 100 μl of 8.5 M acetic acid, and the extinction at 405 nm was determined.

The results of measurement from Examples 1 to 6 were evaluated using a calibration plot obtained by addition of urokinase (Examples 1 to 5) or single-chain tissue plasminogen activator to inhibitor-deficient plasma. The latter was prepared by addition of single-chain tissue plasminogen activator to standard human plasma (40 I.U. (International units)/ml of plasma), incubation at 23° C. for one hour, and subsequent immunoadsorption on anti-tissue plasminogen activator-sepharose. The measured plasminogen activator concentration was then inversely proportional to the plasminogen activator inhibitor concentration.

EXAMPLE 7a Determination of tissue plasminogen activator in plasma

50 μl samples of human plasma which had been supplemented with 10 to 160 IU of single-chain t-PA were incubated with 100 pg of t-PA stimulator (such as, for example, fibrinogen degradation products from the action of plasmin in the presence of 5 mM EDTA) and 1 CTA-U of plasminogen and, for zero balancing, with 0.6 mmol (absolute) of NaCl in 500 μl of basic buffer U and 200 μl of 10 mM chloramine T at 37° C. for 5 min. This was followed by addition of 100 μl of 3 mM H-D-Nva-CHA-Lys-pNA in 1.2 M NaCl or in distilled water (for zero balancing). After incubation at 37° C. for 60 min, the substrate conversion was stopped by addition of 100 μl of 8.5 M acetic acid, and the extinction at 405 nm was measured.

TABLE 7

| Sample | Plasmin activity Extinction/h (mE) |
| --- | --- |
| Normal plasma | 0 ± 2 |
| Normal plasma + 10 IU t-PA/ml | 12 ± 1 |
| Normal plasma + 20 IU t-PA/ml | 20 ± 1 |
| Normal plasma + 40 IU t-PA/ml | 28 ± 2 |
| Normal plasma + 80 IU t-PA/ml | 60 ± 7 |
| Normal plasma + 160 IU t-PA/ml | 221 ± 12 |

Oxidative elimination of alpha$_2$-antiplasmin in the sample permits quantitative measurement of the active tissue plasminogen activator in the plasma.

EXAMPLE 7 Determination of single-chain urinary plasminogen activator (scu-PA) in plasma For this experiment, 100 u-PA units (=1000 ng) of scu-PA were taken up in 1 ml of citrate-treated standard human plasma. Samples containing 100 u-PA units/ml, 10 U/ml, 1 U/ml, 0.1 U/ml and 0.01 U/ml were prepared by dilution with citrate-treated standard human plasma. 50 μl of each sample were incubated with 50 μl of a 30 mM chloramine T solution and 500 μl of solution A at 37° C. for 10 min.

After addition of 100 μl of a chromogenic plasmin substrate and 200 μl of a plasminogen solution (2 CTA-U of plasminogen per 200 μl of a modified solution F which differed from the standard formulation by containing 10 mM tranexamic acid), the sample was incubated at 37° C. for 40 min. After addition of 100 μl of 8.5 M acetic acid, the extinction at 405 nm was determined. The result of the experiment is shown in FIG. 5.

EXAMPLE 8 Determination of the plasminogen concentration in plasma

For the experiment on which this Example is based, a plasminogen-deficient plasma which had been prepared by immunoadsorptive depletion on antiplasminogen-$^R$Sepharose 4B, a citrate-treated standard human plasma containing 3.5 CTA-U/ml plasminogen, a plasma with a high plasminogen content prepared therefrom by addition of plasminogen and containing 23.5 CTA-U/ml plasminogen, and mixtures of the various plasmas which resulted in final concentrations of 1.75 CTA-U/ml, 4.13 CTA-U/ml, 4.75 CTA-U/ml, 6 CTA-U/ml, 8.5 CTA-U/ml and 13:5 CTA-U/ml, were assayed in parallel. For this purpose, 50 μl of each sample was incubated with 500 μl of solution A (basic buffer), 50 μl of a 30 mM chloramine T solution in H20, 50 μl of a 40 mM tranex-amic acid solution in H20, 50 μl of solution C (plasminogen activator reagent) containing 123 units of urokinase per ml, and 200 μl of solution E (plasmin substrate reagent) at 37° C. for 12 min. In parallel, 50 μl of each of the same samples were incubated with 500 μl of solution A (basic buffer), 100 μl of distilled water, 50 μl of solution C (plasminogen activator reagent) containing 123 units of urokinase per ml, and 200 μl of solution E (plasmin substrate reagent), likewise at 37° C.. The reaction in all the samples was then stopped by addition of 100 μl of 8.5 M acetic acid, and the extinction at 405 nm was determined.

Comparison of the values for the plasmas treated with water with the plasma treated according to the invention demonstrates that virtually no change in extinction is observed without addition of the substances according to the invention, i.e. no plasmin activity is detectable. In contrast to this, the plot resulting from the samples treated according to the invention exhibits a linear relation between the plasminogen concentrations in the sample and the extinction at 405 nm. The consequence of this is that the plasminogen concentration in plasma can be determined reliably using the assay system according to the invention.

Comparison Experiment 5 Optimization of the chloramine concentration in the functional PAI (PA) determination a) For chloramine T.

The chloramine T concentrations added in the determination method specified in Example 3 were varied from 0 to 9 mmol/l of reaction mixture. The assayed samples were either a) deficient in functional PAI (=PAI-deficient plasma) or b) rich in functional PAI. An optimum of generated plasmin activity is found on addition of between 1 and 4 mmol/l chloramine T. The two plasma plots are parallel throughout the range, i.e. u-PA/PAI complexes are stable up to at least 9 mM chloramine T in the reaction mixture (=650 l).

b) For chloramine B.

The results which emerge when chloramine B is used in place of chloramine T are the same as represented for chloramine T.

Comparison Experiment 6 Optimization of the tranexamic acid concentration in the functional PAI (PA) determination

Basic buffer (A) and PAI-deficient plasma as samples are examined as in Example 3 for the functional PAI content with varying tranexamic acid concentrations. A maximum is found with 1–4 mM tranexamic acid in the reaction mixture.

Comparison Experiment 7 Optimization of the assay pH for functional PAI (PA) determination

Variation of the pH of the basic buffer U from 7.5 to 9.5 and determination of the functional PAI content of PAI-deficient plasma and PAI-rich plasma as in Example 3 reveals a pH optimum between pH 8.3 and pH 9. However, since the two plots are no longer parallel above pH 8.7, which indicates instability of the u-PA/-PAI complexes, the optimal assay pH is regarded as being pH 8.4.

Comparison Experiment 8 Optimization of the plasminogen concentration in the functional PAI (PA) determination

PAI-deficient plasma is examined as in Example 3 with varying plasminogen concentrations. A saturation plateau is reached with Glu-plasminogen in a concentration of at least 0.9 $\mu$M in the reaction mixture.

Comparison Experiment 9 Optimization of the preincubation time

PAI-deficient plasma, normal plasma and PAI-rich plasma are examined as in Example 3, varying the preincubation time. At least 2 minutes are necessary for complete reaction between PAI and u-PA in the case of normal plasma, while the necessary reaction time increases to 5 minutes in the case of PAI-rich plasma.

Comparison Experiment 10 PAI recovery experiments

PAI-rich plasma (containing 22.5 u-PA inhibiting units/ml) was diluted with PAI-deficient plasma and analyzed as in Example 3. It emerges that each dilution below 14 u-PA inhibiting units (U) of PAI/ml results in a directly propinhibiting ortional linear rise in the measured plasmin activity and thus a directly proportional linear fall in the PAI activity. Plasmas containing more that 14 U of PAI/ml must be diluted with plasmas of known low PAI contents. Below 30% remaining activity of the u-PA used (where there are more than 14 U of PAI/ml), the calibration plot becomes non-linear and approaches the x1 axis asymptotically.

Comparison Experiment 11 Effect of chloramine T and/or tranexamic acid on the functional essay for PAI determination

In order to show that PAI determinations based on the principle according to the invention are independent of plasma alpha$_2$-antiplasmin, PAI standard plasma, that is to say plasmas of known PAI contents, and alpha$_2$-antiplasmindeficient plasma are examined for functional PAI content as in Example 3 with addition of chloramine T and/or tranexamic acid to the reaction mixture. It emerges that sample determination without addition of chloramine T results in generation of plasmin activity which is dependent on the alpha$_2$-antiplasmin content bf the sample. Performing the assay without chloramine T and without tranexamic acid results in complete inhibition of the plasmin generated; virtually no change in extinction can be detected.

However, a plasmin activity was observed with alpha$_2$-anti-plasmin-deficient plasma. Addition of only tranexamic acid resulted in measurable plasmin activities. However, with alpha$_2$-antiplasmin-deficient plasma, these activities about 70% higher than with Lormal plasma, which means that there is dependence on the alpha$_2$-antiplasmin in the sample. The addition of only chloramine T results in an increase in the plasmin activity of 20% compared with normal plasma. This finding demonstrates that the determination of PAI is virtually independent of the alpha$_2$-antiplasmin in the sample. A combination of tranexamic acid and chloramine T generally raises the plasmin activity (effect of tranexamic acid) and an increase of only 5% in the plasmin activity in the case of alpha$_2$-antiplasmin-deficient plasma (effect of chloramine T). Functional PAI determination under these conditions does not depend on the plasma alpha$_2$-antiplasmin concentration. This means that there is a synergistic effect of oxidizing agent and omega-amino carboxylic acid.

TABLE 8

| Addition: | Sample: Normal plasma delta A/4 min | Normal plasma without alpha$_2$-antiplasmin |
|---|---|---|
| distilled water | 40 mA | 217 mA |
| chloramine T | 225 mA | 271 mA |
| tranexamic acid | 488 mA | 829 mA |
| Chloramine T and tranexamic acid | 910 mA | 952 mA |

Comparison Experiment 12 Comparison of methods, coefficient of variation

The determination of PAI according to the invention in the presence of oxidizing agents as in Example 3b was compared with a commercially available functional PAI assay based on the acidification method ($^R$Spectrolyse TM/pL from Biopool, Umea, Sweden). Samples from 20 volunteer donors were measured with both methods. The two methods correlated well with a correlation coefficient of r=0.91. Intra- and interassay coefficients of variation were below 5% with the method according to the invention.

Comparison Experiment 13 Oxidative inactivation of antithrombin III (AT III), oxidation resistance of thrombin

50 pmol of AT III in 50 $\mu$l of 50 mM Tris, 100 mM NaCl, 0.1% (w/v) Triton×100, pH 8.8 buffer, are preincubated with increasing quantities of chloramine T or hydrogen peroxide in 50 $\mu$l of distilled water at 37° C. for 15 min. Then 3 pmol of human alpha-thrombin, 2.5 IU of heparin and 2 KIU of aprotinin in 500 $\mu$l of 100 mM Tris, 150 mM NaCl, pH 8.2, are added, and the mixture is incubated at 37° C. for 5 min. Addition of 500 $\mu$l of 0.4 mM H-D-CHA-But-ArgpNA was followed by further incubation for 3 min (37° C.). The reaction was stopped by 100 μl of 8.5 M acetic acid, and the change in extinction at 405 nm was determined.

Result: Addition of 500 nmol of chloramine T or 500 times the dose of H202 inactivates 50 pmol of AT III without the activity of thrombin being impaired.

Comparison Experiment 14 Stability of serine protease/serine protease inhibitor complexes a) u-PA/AT III complexes 50 pmol of AT III and buffer control is incubated with 1 IU of urokinase in the presence of 5 IU/ml heparin in 175 μl of basic buffer A at 37° C. for 30 min. Then 50 μl of chloramine T of increasing concentration, and 500 μl basic buffer A are added. After 30 min (37° C.), the substrate reaction is started by addition of 200 μl of 2.5 mM chromogenic plasmin substrate H-D-Phe-Tyr-Arg-ANBA and 120 pmol of plasminogen in 200 μl of basic buffer A. After 15 min (37° C.), the reaction was stopped by 100 μl of 8.5 M acetic acid, and the change in extinction at 405 nm was determined.

Result: Compared with the buffer control there is found to be a constant loss of activity, caused by u-PA complexation, in the sample containing AT III and u-PA, irrespective of added CT, that is to say u-PA/AT III complexes are resistant to oxidation.

b) Plasmin/antiplasmin complexes 30 pmol of alpha$_2$-antiplasmin and basic buffer A (control mixture) are incubated with 50 pmol of plasmin in 175 μl of basic buffer A for 5 min (37° C.). Addition of 500 μl of chloramine T of various concentrations in basic buffer A is followed by incubation for 30 min (37° C.), and the detection reaction is started by addition of 200 μl of 2.5 mM chromogenic plasmin substrate H-D-Phe-Tyr-Arg-ANBA in basic buffer A. After 3 min (37° C.), the reaction is stopped by addition of 100 μl of 8.5 M acetic acid, and the change in extinction at 405 nm is determined. No additional plasmin activity is generated even by chloramine T concentrations above 5 mM in the reaction mixture, that is to say plasmin/antiplasmin complexes are oxidation-resistant.

We claim:

1. A method for the determination of the activity of serine proteases or serine protease inhibitors in a sample of plasma or other biological fluids comprising the steps of:
   (i) adding at least one oxidizing agent to said sample which oxidizes methionine to methionine sulfoxide at a pH of 7.5 to 8.8;
   (ii) adding simultaneously o rafter a preincubation period a plasminogen activator and a first substrate for said plasminogen activator, said first substrate being activated by a said plasminogen activator to yield an enzyme which can be detected by means of a second substrate; and
   (iii) bringing said activated first substrate into contact with said second substrate which second substrate can be detected after conversion by said activated first substrate.

2. The method of claim 1, wherein said serine protease inhibitors are plasminogen activator inhibitors.

3. The method of claim 1, further comprising the steps, of:
   (iv) adding a defined quantity of plasminogen activator to said sample; and
   (v) determining the quantity of plasminogen activator inhibitor by computing the deference of the activity of added plasminogen activator activity and the remaining plasminogen activator activity after inhibition by said plasminogen activator inhibitor contained in said sample.

4. The method of claim 1, wherein said detection after conversion by said activated first substrate is conducted by photometric means.

5. The method of claim 1, wherein said serine protease is a plasminogen activator, plasmin or thrombin.

6. The method of claim 1, wherein said oxidizing agent is selected from the group consisting of halogeno amines and salts thereof, halogeno imines and salts thereof, halogeno amides and salts thereof, halogeno imides and salts thereof, and halogeno hydroxyls and salts thereof.

7. The method of claim 1, wherein said oxidizing agent is selected form the group consisting of hydrogen peroxide, salts of peroxomonosulfuric acid, salts of peroxodisulfuric acid, oxidized gluthathione, chloramine t, chloramine B, salts of HOCl and N-chlorosuccinimide.

8. The method of claim 1, further comprising the step of adding at least one omega-amino carboxylic acid prior to step (ii).

9. The method of claim 1, further comprising the step of adding at least one detergent prior to step (ii).

10. The method of claim 1, further comprising the step of adding at least one omega-amino carboxylic acid and at least one detergent to said sample prior to step (ii).

11. The method of claim 1, wherein said first substrate is plasminogen or one of its natural or synthetic derivatives.

12. The method of claim 1, wherein said first substrate is miniplasminogen.

13. The method of claim 1, wherein said second substrate is plasmin.

14. The method of claim 2, wherein said serine protease is selected form the group consisting of a plasminogen activator, plasmin and thrombin.

15. The method of claim 2, wherein said oxidizing agent is selected from the group consisting of halogeno amines and salts thereof, halogeno imines and salts thereof, halogeno amides and salts thereof, halogeno imides and salts thereof, and halogeno hydroxyls and salts thereof.

16. The method of claim 2, wherein said oxidizing agent is selected from the group consisting of hydrogen perioxide, salts of peroxomonosulfuric acid, salts of peroxodisulfuric acid, oxidized gluthathione, chloramine T, chloramine B, salts of HOCl and N-chlorosuccinimide.

17. The method of claim 2, further comprising the step of adding at least one omega-amino carboxylic acid prior to step (ii).

18. The method of claim 2, further comprising the step of adding at least one detergent prior to step (ii).

19. The method of claim 2, further comprising the step of adding at least one omega-amino carboxylic acid and at least one detergent to said sample prior to step (ii).

20. The method of claim 2, wherein said serine protease inhibitor is a placental type plasminogen activator inhibitor (2) further comprising the step of adding polycation to said sample.

21. The method of claim 2, wherein said polycations are protamine chloride.

22. The method of claim 2, wherein said serine protease is a single chain urokinase.

23. The method of claim 2 further comprising the step of adding kallikrein or a surface activator to said sample simultaneously with said oxidizing agent or after said preincubation period.

* * * * *

UNITED STATES PATENT AND TRADEMARK OFFICE
CERTIFICATE OF CORRECTION

PATENT NO. : 5,057,414

DATED : October 15, 1991

INVENTOR(S) : Thomas STIEF et al.

It is certified that error appears in the above-identified patent and that said Letters Patent is hereby corrected as shown below:

Abstract, line 13, change "and" to --the--.

Claim 1, column 17, line 49, change "o rafter" to --or after--.

Claim 1, colum 17, line 52, after "by" Delete "a".

Claim 3, column 17, line 66, change "deference" to --difference--.

Claim 7, column 18, line 14, change "form" to --from--.

Claim 7, column 18, line 17, change "t" to --T--.

Claim 12, column 18, line 30, change "1" to --11--.

UNITED STATES PATENT AND TRADEMARK OFFICE
CERTIFICATE OF CORRECTION

PATENT NO. : 5,057,414

DATED : October 15, 1991

INVENTOR(S) : Thomas STIEF et al.

It is certified that error appears in the above-identified patent and that said Letters Patent is hereby corrected as shown below:

Claim 14, column 18, line 34 and 35, change "proease" to --protease--.

Claim 14, column 18, line 35, change "proease" to --protease--.

Claim 14, column 18, line 35, change "form" to --from--.

Claim 16, column 18, line 44, change "perioxide" to --peroxide--.

Claim 20, column 18, line 59, change "polycation" to --polycations--.

UNITED STATES PATENT AND TRADEMARK OFFICE
CERTIFICATE OF CORRECTION

PATENT NO. : 5,057,414

DATED : October 15, 1991

INVENTOR(S) : Thomas Stief etal

It is certified that error appears in the above-identified patent and that said Letters Patent is hereby corrected as shown below:

Claim 21, column 18, line 61, change "2" to --20--.

Signed and Sealed this

Twenty-fourth Day of November, 1992

Attest:

DOUGLAS B. COMER

*Attesting Officer*   *Acting Commissioner of Patents and Trademarks*